US011400087B2

(12) United States Patent
Raoufinia

(10) Patent No.: US 11,400,087 B2
(45) Date of Patent: *Aug. 2, 2022

(54) METHOD OF PROVIDING ARIPIPRAZOLE TO PATIENTS HAVING IMPAIRED CYP2D6 OR CYP3A4 ENZYME FUNCTION

(71) Applicant: Otsuka Pharmaceutical Co., Ltd., Rockville, MD (US)

(72) Inventor: Arash Raoufinia, Vienna, VA (US)

(73) Assignee: Otsuka Pharmaceutical Co., Ltd., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/304,606

(22) Filed: Jun. 23, 2021

(65) Prior Publication Data

US 2021/0308127 A1 Oct. 7, 2021

Related U.S. Application Data

(63) Continuation of application No. 17/206,241, filed on Mar. 19, 2021, which is a continuation of application No. 16/710,495, filed on Dec. 11, 2019, now Pat. No. 10,980,803, which is a continuation of application No. 14/034,727, filed on Sep. 24, 2013, now Pat. No. 10,525,057.

(51) Int. Cl.
```
A61K 31/496     (2006.01)
A61K 45/06      (2006.01)
A61K 47/26      (2006.01)
A61K 9/00       (2006.01)
A61K 9/10       (2006.01)
A61P 25/00      (2006.01)
A61K 9/19       (2006.01)
```

(52) U.S. Cl.
CPC .......... A61K 31/496 (2013.01); A61K 9/0019 (2013.01); A61K 9/10 (2013.01); A61K 45/06 (2013.01); A61K 47/26 (2013.01); A61P 25/00 (2018.01); A61K 9/19 (2013.01)

(58) Field of Classification Search
CPC .... A61K 31/4704; A61K 31/495; A61P 25/18
See application file for complete search history.

(56) References Cited

U.S. PATENT DOCUMENTS

| | | | |
|---|---|---|---|
| 4,282,233 | A | 8/1981 | Vilani |
| 4,659,716 | A | 4/1987 | Villani et al. |
| 4,734,416 | A | 3/1988 | Banno et al. |
| 5,006,528 | A | 4/1991 | Oshiro et al. |
| 6,559,128 | B1 | 5/2003 | Hamm et al. |
| 6,669,963 | B1 | 12/2003 | Kampinga |
| 7,115,587 | B2 | 10/2006 | Naringrekar et al. |
| 7,807,680 | B2 | 10/2010 | Kostanski et al. |
| 8,030,313 | B2 | 10/2011 | Kostanski et al. |
| 8,338,427 | B2 | 12/2012 | Brown |
| 8,431,576 | B2 | 4/2013 | Remenar et al. |
| 10,525,057 | B2 * | 1/2020 | Raoufinia ............ A61K 31/496 |
| 10,980,803 | B2 * | 4/2021 | Raoufinia ................ A61K 9/10 |
| 11,154,553 | B1 * | 10/2021 | Raoufinia ............ A61K 9/0019 |
| 2002/0106403 | A1 | 8/2002 | Parik et al. |
| 2005/0032811 | A1 | 2/2005 | Brown et al. |
| 2005/0148597 | A1 * | 7/2005 | Kostanski ............ A61K 31/497 514/253.07 |
| 2009/0022823 | A1 | 1/2009 | Ehrich et al. |
| 2010/0004262 | A1 * | 1/2010 | Wilding .................. A61P 25/28 514/253.07 |

FOREIGN PATENT DOCUMENTS

| | | |
|---|---|---|
| EP | 1330249 | 7/2003 |
| WO | WO 97/44039 | 11/1997 |
| WO | WO 99/25354 | 5/1999 |
| WO | WO 03/026659 | 4/2002 |

OTHER PUBLICATIONS

Kane et al., (J. Clin. Psychiatry vol. 73 pp. 617-624. Published 2012). (Year: 2012).*
Ability Maintena clinical pharmacology review (disclosed to the public on May 14, 2012) (Year: 2012).*
Ability label dated Feb. 22, 2012.
Hendset et al.; "Impact of the CYP2D6 genotype on steady-state serium, concentrations of aripiprazaole and dehydroaripiprazole;" Eur J. Clin Pharmacol; 2007; 63: 1147-1151.
Abilify Maintena (package insert). Tokyo, Japan: Otsuka Pharmaceutical Co., Ltd. 2013. Available from: http//www.otsuka-us.com/Products/Documents/Abilify.M.PI.pdf.
Kane et al., J. Clin. Psychiatry, May 2012; 73(5): 617-624.
In re Cyclobenzaprine Hydrochloride Extended-Release Capsule Patent Litigation, 676 F.3d 1063 (2012), Unites States Court of Appeals, Federal Circuit.
ASISTADA Prescribing Information; (Reference ID 3829516), revised Oct. 2015, pp. 1-31, Alkermes, Inc., U.S.A.
Gopalakrishna et al., Long-Acting Injectable Aripiprazole: How Might It Fit Into Our Tool Box?, Jul. 10, 2013, Clinical Schizophrenia and Related Psychoses, pp. 87-92.
Bertilsson et al. Molecular geneticcs of CYP2D6: Clinical relevance with focus on pyschotrophic drugs, 2002, Br. J. Clin. Pharmacol, vol. 53, pp. 111-122.
Fleischhacker et al., A pharmacokinetic study of once-monthly aripiprazole extended-release injectable suspension (ERIS) in adult patients with schizophrenia, 2011, 164th Annu.
Park et al., Aripiprazole treatment for patients with schizophrenia: from acute treatment to maintenance treatment, 2011, Expert Rev Neurother, vol. 11, No. 11, pp. 1541-1552.
Sparshatt et al., A Systematic Review of Aripiprazole-Dose, Plasma Concentration, Receptor Occupancy, and Response Implications for Therapeutic Drug Monitoring, 2010, J Clin P.

(Continued)

*Primary Examiner* — Theodore R. Howell
*Assistant Examiner* — George W Kosturko
(74) *Attorney, Agent, or Firm* — Finnegan, Henderson, Farabow, Garrett & Dunner, LLP

(57) ABSTRACT

The disclosed embodiments relate to methods of initiating aripiprazole treatment in a patient who is a CYP2D6 poor metabolizer or a CYP3A4 poor metabolizer, or both.

30 Claims, 2 Drawing Sheets

(56) References Cited

OTHER PUBLICATIONS

Azuma et al., The relationship between clinical pharmacokinetics of aripiprazole and CYP2D6 genetic polymorphism: effects of CYP enzyme inhibition by coadministration of parox.
Davis et al. Depot Antipsychotic Drugs, Place in Therapy, in Drugs (1994, 47(5): pp. 741-773).
Floyd et al., Injectable Emulsions and Suspensions, in Pharmaceutical Dosage Forms. Disperse Systems Ch. 7 (H.A. Lieberman et al. eds., 2d ed. 1996).
Ma et al., New Developments in Particle Characterization by Laser Diffraction: Size and Shape, 111 Powder Technology 66 (2000).
Nema et al. (51(4) PDA J. of Pharm. SCU, & Tech. 166-171 (1970).
Aoki, Study on Crystal Transformation of Aripiprazol, Fourth Japan-Korea Symposium on Separation Technology, published 1996.
Cocoman et al., Intramuscular Injections: A Review of Best Practice for Mental Health Nurses, 15(5) Journal of Psychiatric and Mental Health Nursing 424 (2008).
The FDA Guide to Inspections of Lyophilization of Parentals, Jul. 1993.
Annual Comprehensive List of Guidance Documents at the Food and Drug Administration, one version of which was published on Oct. 24, 2001 under 21 CFR 10.115(n)(2), https://www.federalregister. gov/documents/2001/10/24/01-26650/annual-comprehensive-list-of-guidance-documents-at-the-food-and-drug-administration.
Particle Size Analysis-Laser Diffraction Methods, ISO Standard 13320-1 (Nov. 10, 1999).
Kane et al., Aripiprazole Intramuscular Depot as Maintenance Treatment in Patients with Schizophrenia: A 52-Week, Multicenter, Randomized, Double-Blind, Placebo-Controlled Study, 73(5) J. Clin. Psychiatry 617 (2012).
Kubo et al., Influence of Itraconazole Co-administration and CYP2D6 Genotype on the Pharmacokinetics of the New Antipsychotic Aripiprazole, 20(1) Drug Metab. Pharmacokinet. 55 (2005).
Malvern 2600 Instruction Manual, Nov. 1991.
EP 1330249 file history, Letter of Observation (Feb. 2, 2004).
Eugene L. Parrott, Milling of Pharmaceutical Solids, 63(6) J. Pharmaceutical Scis. 813 (1974).
Particular Matter in Injections, <788>, United States Pharmacopeia 1813-19 (USP 23 1995).
Waade et al., Influence of Comedication on Serum Concentrations of Aripiprazole and Dehydroaripiprazole, 21 Ther. Drug Monit 233 (2009).
Broadhead, Parental Dosage Forms, Pharmaceutical Preformulation and Formulation (Mark Gibson ed., 2001).
Potkin et al., Safety and Tolerability of Once Monthly Aripiprazole Treatment Initiation in Adults with Schizophrenia Stabilized on Selected Atypical Oral Antipsychotics other than Aripiprazole, 29(10) Current Medical Research & Opinion 1241 (2013).

\* cited by examiner

METHOD OF PROVIDING ARIPIPRAZOLE TO PATIENTS HAVING IMPAIRED CYP2D6 OR CYP3A4 ENZYME FUNCTION

This is a continuation of U.S. application Ser. No. 17/206, 241, filed on Mar. 19, 2021, which is a continuation of U.S. application Ser. No. 16/710,495, filed Dec. 11, 2019, now U.S. Pat. No. 10,980,803, issued Apr. 20, 2021, which is a continuation of U.S. application Ser. No. 14/034,727, filed Sep. 24, 2013, now U.S. Pat. No. 10,525,057, issued on Jan. 7, 2020; the contents of each application are incorporated herein by reference in its entirety.

BACKGROUND

Aripiprazole can be administered to treat schizophrenia, bipolar mania (e.g., bipolar I disorder), depression, irritability associated with autistic disorder, agitation associated with schizophrenia or bipolar I disorder, and other psychological disorders. For some patients, once a day administration of a dosage form that systemically releases aripiprazole can be problematic, because patients with these disorders may be unwilling or unable to take medication every day. An intramuscular depot formulation that systemically releases aripiprazole over a long period of time can be helpful. However, once the intramuscular depot is administered, adjusting the dosage to account for variations in the patient population is difficult.

SUMMARY OF THE INVENTION

In various embodiments, the present invention is directed to methods of systemically delivering aripiprazole to a patient, particularly patients having impaired CYP2D6 or CYP3A4 enzyme function. In one embodiment, the present invention comprises administering intramuscularly to a patient, a starting dose of a long-acting drug-containing suspension which systemically releases therapeutic plasma levels of aripiprazole over a period of about one month to a patient, wherein said patient has impaired CYP2D6 or CYP3A4 enzyme function. Patients with impaired CYP2D6 or CYP3A4 enzyme function include, for example a patient who is a CYP2D6 or CYP3A4 poor metabolizer, a patient concomitantly administered a strong CYP3A4 and/or CYP2D6 inhibitor, or a patient who is a CYP2D6 or CYP3A4 poor metabolizer and is concomitantly administered a strong CYP3A4 and/or CYP2D6 inhibitor. In various embodiments, the dose of long-acting drug-containing suspension providing therapeutic plasma levels of aripiprazole administered to such patient with impaired CYP2D6 or CYP3A4 enzyme function is adjusted such that the starting dose provides no more than about 75%, about 75%, no more than about 50%, about 66% to about 75%, or about 50%, of the amount of aripiprazole compared to an initial dose recommended for a patient with normal CYP2D6 and CYP3A4 enzyme function (i.e., who is neither a CYP2D6 poor metabolizer nor a CYP3A4 poor metabolizer and is not concomitantly administered a CYP2D6 or CYP3A4 inhibitor or inducer, or other agents which modify CYP2D6 or CYP3A4 function). In other embodiments, the patient with impaired CYP2D6 or CYP3A4 enzyme function is a CYP2D6 or CYP3A4 poor metabolizer. In still other embodiments the patient with impaired CYP2D6 or CYP3A4 enzyme function is a CYP2D6 poor metabolizer. In still other embodiments the patient with impaired CYP2D6 or CYP3A4 function is a CYP3A4 poor metabolizer. In some embodiments, the patient with impaired CYP2D6 or CYP3A4 enzyme function is an extensive metabolizer who has been concomitantly administered a strong CYP2D6 inhibitor or a strong CYP3A4 inhibitor. In some embodiments, the patient with impaired CYP2D6 or CYP3A4 enzyme function is an extensive metabolizer who has been concomitantly administered both a strong CYP2D6 inhibitor and a strong CYP3A4 inhibitor. In yet other embodiments, the patient is schizophrenic and/or aripiprazole naïve. In particular embodiments, the starting dose of the present method systemically releases no more than about 160 mg, no more than about 200 mg, or no more than about 300 mg of aripiprazole per dose. In some embodiments, the patient is coadministered an oral antipsychotic for at least the first 14 days after administration of said starting dose of the long-acting drug containing suspension. In some embodiments the long-acting drug-containing suspension comprises aripiprazole or a prodrug thereof. In some embodiments, the long-acting, drug containing suspension comprises s (7-(4-(4-(2,3-dichlorophenyl)piperazin-1-yl)butoxy)-2-oxo-3,4-dihydroquinolin-1(2H)-yl)methyl dodecanoate.

DETAILED DESCRIPTION OF THE INVENTION

Throughout the disclosure, singular forms such as "a," "an," and "the" are often used for convenience. However, it should be understood that the singular forms are intended to include the plural, except when context or an explicit statement indicates that the singular alone is intended. It should also be understood that all patents, publications, journal articles, and the like that are mentioned in this Application are incorporated by reference in their entirety and for all purposes.

Figure 1:
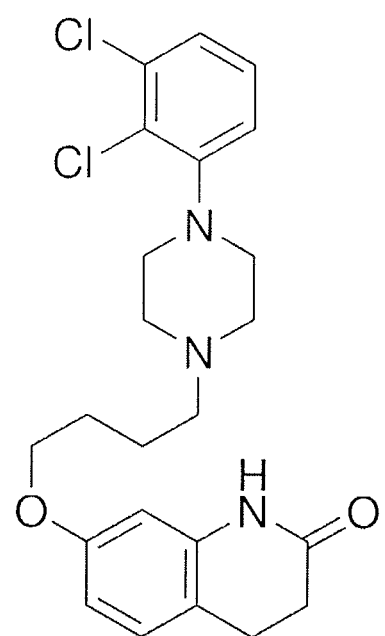
FIG. 1 is the chemical structure of aripiprazole.

"Aripiprazole" includes the compound 7-(4-[4-(2,3-dichlorophenyl)piperazin-1-yl]butoxy-3,4-dihydroquinolin-2 (1H)-one, the structure of which is shown in FIG. 1, as well as pharmaceutically acceptable salts thereof.

"Initiating aripiprazole treatment" includes starting a patient on a particular dosing or medication regime involving systemically delivering aripiprazole to a patient. At the time of initiating aripiprazole treatment, the patient may have been previously treated with another drug, or by aripiprazole under a different dosing regime.

An "aripiprazole prodrug" or "prodrug of aripiprazole" is a molecule that releases aripiprazole by forming aripiprazole or its active metabolite (i.e., dehydroaripiprazole) in situ in the body of a patient.

A "patient" is a living organism, typically a human.

"Long-acting" refers to drug compositions that provide or release clinically effective amounts of one or more drugs, particularly aripiprazole, over an extended period of time, typically over a time period of about one week to about one month.

A formulation which "releases" aripiprazole or an "aripiprazole-releasing" formulation refers to a formulation which contains aripiprazole itself, or a formulation which contains a prodrug (e.g., (7-(4-(4-(2,3-dichlorophenyl)piperazin-1-yl)butoxy)-2-oxo-3,4-dihydroquinolin-1(2H)-yl)

methyl dodecanoate) or other form of aripiprazole which forms aripiprazole in situ in the body of a patient.

When the amount of a component of a composition or formulation is expressed as a percentage, the percentage is a weight/weight percentage based on the total weight of the composition or formulation unless otherwise specified.

All terms not specifically defined herein should be given the ordinary meaning that a person of skill in the art at the time of the invention would ascribe to them.

Atypical antipsychotic drugs such as aripiprazole are used to treat chronic conditions such as schizophrenia, and therefore a typical patient will be dosed with aripiprazole over long periods of time (often lifelong). It is important that the aripiprazole plasma levels in a patient be maintained within an appropriate therapeutic range in order to maximize the clinical benefit (i.e., control of schizophrenic symptoms, preventing mania, stabilizing mood, etc.), while minimizing potentially serious extrapyramidal side effects such as tardive dyskinesia. Doses which are too low can provide ineffective treatment of, e.g. schizophrenic symptoms, which can be disastrous to a patient's quality of life, while doses which are too high can cause serious and sometimes irreversible side effects. Because the plasma levels of aripiprazole can be significantly affected by the rate at which the drug is metabolized in the patient, it is important to account for the CYP2D6 and CYP3A4 isozyme function of a patient in order to achieve the desired, clinically effective plasma levels of aripiprazole, while minimizing side effects.

Many drugs are metabolized in the liver by one or more of the cytochrome P450 (CYP) family of enzymes. Aripiprazole is primarily metabolized by the CYP2D6 and CYP3A4 isozymes. These isozymes often exhibit significant phenotypic variability, which can significantly affect the functioning of the enzyme. Most patients can be characterized as having "normal" CYP2D6 or CYP3A4 enzyme function, and readily ("extensively") metabolize drugs such as aripiprazole. However, some patients have little or no CYP2D6 or CYP3A4 enzyme function, and can be considered "poor metabolizers"—i.e., have a substantially reduced ability to metabolize aripiprazole, and therefore do not eliminate it as efficiently as extensive metabolizers. Such "poor metabolizers" may have about an about 63-112% increase in aripiprazole exposure (an average of about 80%) and about a 35% decrease in exposure to the active metabolite of aripiprazole, compared to the extensive metabolizers.

Some drugs or foods act as inhibitors for CYP2D6 or CYP3A4 enzymes, and therefore can inhibit or reduce the metabolism of aripiprazole if concomitantly administered or consumed within the time-frame that aripiprazole is administered, for example shortly before or after administration of aripiprazole. Such drugs or foods are referred to as CYP2D6 or CYP3A4 inhibitors. Similar to the effects observed for poor metabolizers, above, extensive metabolizers concomitantly administered CYP2D6 inhibitors and/or CYP3A4 inhibitors also exhibit an approximately 63-112% increase in aripiprazole exposure (average of about 80%) and about a 35% decrease in exposure to the active metabolite of aripiprazole. Concomitant administration of such inhibitors with compositions which release aripiprazole (e.g., long-acting intramuscular depot compositions which systemically release aripiprazole) can be particularly important when the patient is also a CYP2D6 or CYP3A4 poor metabolizer, since the metabolism of aripiprazole will be suppressed by the poor metabolizer's innately low CYP2D6 or CYP3A4 enzyme activity, as well as the further inhibition provided by the CYP2D6 or CYP3A4 inhibitor. Poor metabolizers concomitantly administered CYP2D6 and/or CYP3A4 inhibitors exhibit a correspondingly greater increase in aripiprazole exposure up to 4 fold in aripiprazole concentrations.

Alternatively, some drugs can significantly increase the activity of the enzyme (e.g., act as "inducers" of the CYP2D6 or CYP3A4 enzyme), and thereby substantially increase the rate of aripiprazole metabolism. Even for patients who are CYP2D6 or CYP3A4 poor metabolizers, the increased rate of metabolism of aripiprazole provided by concomitantly administered "inducers" may be such that intramuscular administration of an aripiprazole-releasing suspension never provides a patient with clinically effective levels of aripiprazole.

Thus, a patient with normal CYP2D6 and CYP3A4 enzyme function is an extensive metabolizer of CYP2D6 and CYP3A4 who is not concomitantly administered either inhibitors or inducers of CYP2D6 or CYP3A4. A patient with impaired CYP2D6 or CYP3A4 (or both) enzyme function includes patients who are CYP2D6 and/or CYP3A4 poor metabolizers, patients who are extensive metabolizers administered strong CYP2D6 and/or CYP3A4 inhibitors, and patients who are CYP2D6 and/or CYP3A4 poor metabolizers concomitantly administered strong CYP2D6 and/or CYP3A4 inhibitors.

Aripiprazole is typically administered as a conventional once-daily oral dosage form (e.g., a tablet) or a once-daily, immediate release injectable solution (which is distinct from the injectable depot formulations of the present method which provide sustained systemic release of aripiprazole over a significant period of time, e.g. about one month). Aripiprazole dosing is readily adjusted in once-daily formulations by appropriately increasing or decreasing the subsequent daily dose. However, some schizophrenic patients may resist or evade complying with the recommended oral dosing regime, or otherwise have difficulty in complying with regular dosing, which can make optimal treatment difficult. Treatment of such patients can be improved by administering a long-acting, injectable intramuscular depot formulation. The intramuscular depot formulation slowly releases clinically effective levels of aripiprazole into the bloodstream (plasma) of the patient over about a month, and therefore avoids compliance issues related to daily dosing. In addition, because the intramuscular depot formulation is injected, it must typically be administered by the treating physician, (rather than by the patient him/herself, as for oral dosage forms), further ensuring patient compliance.

Dosing for oral and intramuscular depot formulations differs in that the drug from an oral formulation is released in the digestive tract and absorbed through the hepatic portal system where the drug can be metabolized by hepatic enzymes (e.g., CYP2D6 and CYP3A4) before it is distributed systemically through the patient. In contrast, intramuscular depot formulations release the drug directly into the patient's bloodstream over an extended period, thereby avoiding initial hepatic enzyme metabolism. Accordingly, the drug exposure provided by an intramuscular depot formulation would not be expected to be the same as that of an oral formulation. Thus dose adjustments suitable for patients with impaired CYP2D6 and/or CYP3A4 enzyme function are not the same as those suitable for patients treated with aripiprazole releasing depot formulations.

In addition, because an intramuscular depot formulation is administered so infrequently (e.g., monthly), dose adjustments cannot be made as readily as for once-daily formulations, and any problems with over- or under-dosing cannot be rectified rapidly. Accordingly, there is a risk that administration of an inappropriate dose of a drug provided in the form of an intramuscular depot formulation would result in extended periods of under-dosing or over-dosing before the optimal dose was achieved, with the consequent risks to the patient's quality of life or exposure to the risk of serious side effects. Thus, there is a need for methods of initiating treatment with aripiprazole-releasing depot formulations that provide an appropriate aripiprazole starting dose to patients, particularly patients with impaired CYP2D6 or CYP3A4 enzyme function.

The starting dose of aripiprazole released from an intramuscularly administered dosage form for a patient with impaired CYP2D6 or CYP3A4 enzyme function, for example a patient who is a CYP2D6 or CYP3A4 poor metabolizer, according to the present method, can be described in reference to the initial dose recommended for a patient with normal CYP2D6 and CYP3A4 enzyme function. For example, the recommended initial dose of an intramuscularly administered depot dosage form which releases aripiprazole systemically into a patient with normal CYP2D6 or CYP3A4 enzyme function is typically about 400 mg or about 300 mg (expressed as an equivalent weight of aripiprazole).

For a patient with impaired CYP2D6 or CYP3A4 enzyme function who is a CYP2D6 poor metabolizer or CYP3A4 poor metabolizer, the starting dose according to the present method would be about 75% of the recommended initial dose of 400 mg of aripiprazole for a patient with normal CYP2D6 or CYP3A4 enzyme function (i.e., about 300 mg, expressed as an equivalent weight of aripiprazole). For a patient with impaired CYP2D6 or CYP3A4 enzyme function who is a CYP2D6 poor metabolizer or a CYP3A4 poor metabolizer, and is concomitantly administered a strong CYP2D6 or CYP3A4 inhibitor, (in particular, patients who are CYP2D6 or CYP3A4 poor metabolizers and concomitantly administered a strong CYP2D6 or CYP3A4 inhibitor for about 14 days or more during treatment with a long-acting drug-containing suspension which delivers therapeutic plasma levels of aripiprazole) the starting dose according to the present method would be about 50% of the recommended initial dose of 400 mg of aripiprazole for a patient with normal CYP2D6 or CYP3A4 enzyme function (i.e. about 200 mg, expressed as an equivalent weight of aripiprazole).

In alternative embodiments, the patient with impaired CYP2D6 or CYP3A4 enzyme function can be an extensive metabolizer (rather than a CYP2D6 or CYP3A4 poor metabolizer), who is concomitantly administered a strong CYP2D6 or CYP3A4 inhibitor, in particular, patients who are extensive metabolizers and concomitantly administered a strong CYP2D6 or CYP3A4 inhibitor for about 14 days or more during treatment with a long-acting drug-containing suspension which delivers therapeutic plasma levels of aripiprazole. For such patients, the starting dose can provide about 66% to about 75%, for example, about 66% of the amount of aripiprazole compared to the initial dose recommended for a patient with normal CYP2D6 and CYP3A4 enzyme function or about 75% of the amount of aripiprazole compared to the initial dose recommended for a patient with normal CYP2D6 and CYP3A4 enzyme function. If the recommended initial dose for a patient with normal CYP2D6 or CYP3A4 enzyme function is 400 mg of aripiprazole, the starting dose for a patient with impaired CYP2D6 or CYP3A4 enzyme function who is an extensive metabolizer concomitantly administered a strong CYP2D6 or CYP3A4 inhibitor according to the present method would be about 75% of the recommended initial dose (i.e., about 300 mg, expressed as the equivalent weight of aripiprazole). If the recommended initial dose for a patient with normal CYP2D6 or CYP3A4 enzyme function is 300 mg of aripiprazole, the starting dose for a patient with impaired CYP2D6 or CYP3A4 enzyme function who is an extensive metabolizer concomitantly administered a strong CYP2D6 or CYP3A4 inhibitor according to the present method would be about 66% of the recommended initial dose (i.e., about 200 mg, expressed as the equivalent weight of aripiprazole).

In yet other embodiments, the patient with impaired CYP2D6 or CYP3A4 enzyme function can be an extensive metabolizer (rather than a CYP2D6 or CYP3A4 poor metabolizer), who is concomitantly administered both a strong CYP2D6 and a strong CYP3A4 inhibitor. If the recommended initial dose for a patient with normal CYP2D6 or CYP3A4 enzyme function is 400 mg of aripiprazole, the starting dose for a patient with impaired CYP2D6 or CYP3A4 enzyme function who is an extensive metabolizer concomitantly administered both a strong CYP2D6 and a strong CYP3A4 inhibitor according to the present method would be about 50% of the recommended initial dose (i.e., about 200 mg, expressed as the equivalent weight of aripiprazole). If the recommended initial dose for a patient with normal CYP2D6 or CYP3A4 enzyme function is 300 mg of aripiprazole, the starting dose for a patient with impaired CYP2D6 or CYP3A4 enzyme function who is an extensive metabolizer concomitantly administered both a strong CYP2D6 and a strong CYP3A4 inhibitor according to the present method would be about 53% of the recommended initial dose (i.e., about 160 mg, expressed as the equivalent weight of aripiprazole).

In still other embodiments, a patient taking a CYP2D6 or CYP3A4 inducer, should entirely avoid intramuscularly administered dosage forms which release aripiprazole.

The intramuscular administration step can involve any suitable form of intramuscular administration, and is most commonly intramuscular injection. The injection can be to any suitable muscle, such as the deltoid muscle, the vastus lateralis muscle, or a gluteal muscle, for example, the ventrogluteal or dorsogluteal muscle.

Figure 2:
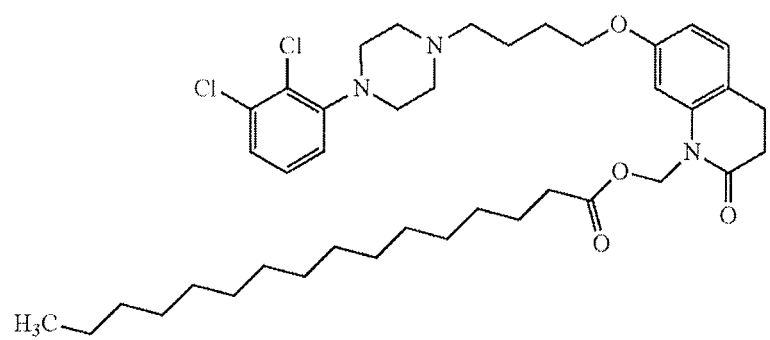
FIG. 2 is a the chemical structure of the aripiprazole prodrug (7-(4-(4-(2,3-dichlorophenyl)piperazin-1-yl)butoxy)-2-oxo-3,4-dihydroquinolin-1(2H)-yl)methyl dodecanoate.

The long-acting drug-containing suspension can comprise aripiprazole or a prodrug thereof. Many aripiprazole prodrugs are known in the art and are disclosed, for example, in U.S. Pat. Pub. 2011/0003828, U.S. Pat. Pub. 2011/0015156 (now U.S. Pat. No. 8,431,576), U.S. Pat. Pub. 2011/0178068, U.S. Pat. Pub. 20110151711, U.S. Pat. Pub. 2012/0202823, U.S. Pat. Pub. 2012/0238552, and U.S. Pat. Pub. 2013/0053301. Particular prodrugs include those disclosed in U.S. Pat. Pub. 2011/0015156 (now U.S. Pat. No. 8,431,576), such as (7-(4-(4-(2,3-dichlorophenyl)piperazin-1-yl)butoxy)-2-oxo-3,4-dihydroquinolin-1(2H)-yl)methyl dodecanoate, the structure of which appears on FIG. 2.

The aripiprazole or prodrug thereof can have a mean particle size of about 1 to about 30 microns, such as about 1 to about 20 microns, about 1 to about 15 microns or about 2 to about 4 or about 2.5 microns in order to provide or release aripiprazole systemically such that a therapeutic plasma level of aripiprazole in the subject is obtained over a period of about one month.

In addition to the aripiprazole or prodrug thereof, the long-acting drug-containing suspension can comprise a solvent for injection and a vehicle for the aripiprazole or prodrug thereof. The solvent for injection can comprise water, for example in the form of Ringer's solution, isotonic sodium chloride solution, etc. In other embodiments, the solvent can comprise an oil, such as natural or synthetic mono- or diglycerides, fatty acids, etc.

The vehicle can include one or more of at least one suspending agent, at least one bulking agent, at least one buffer, and at least one pH adjusting agent. Exemplary vehicles are disclosed in U.S. Pat. No. 8,030,313.

The at least one suspending agent, when used, can be present in an amount of from about 0.2% to about 10%, such as from about 0.5% to about 5%. Exemplary suspending agents are disclosed in U.S. Pat. No. 8,030,313. Particular exemplary suspending agents include carboxymethyl cellulose or its sodium salt.

The at least one bulking agent, when used, can be present in an amount of from about 1% to about 10%, such as about 3% to about 8%, or about 4% to about 5%. Exemplary bulking agents are disclosed in U.S. Pat. No. 8,030,313. Particular exemplary bulking agents are sorbitol and xylitol.

The at least one buffer, when used, can be used in amount required to adjust the pH of an aqueous suspension from a pH of about 6 to about 8, such as about 7, and can be incorporated into the aqueous suspension in an amount of from about 0.02% to about 2%, about 0.03% to about 1%, or about 0.1%. Exemplary buffers are also disclosed in U.S. Pat. No. 8,030,313. Particular exemplary buffers include sodium phosphate, potassium phosphate, and TRIS.

The at least one pH adjusting agent, when used, can be used in an amount required to adjust the pH from about 6 to about 7.5, such as about 7. The pH adjusting agent can be an acid, such as hydrochloric acid, when the pH must be lowered or a base, such as sodium hydroxide, when the pH must be raised. Exemplary pH adjusting agents are also disclosed in U.S. Pat. No. 8,030,313.

In other embodiments, the long-acting drug-containing suspension can comprise aripiprazole or a prodrug of aripiprazole, which in either case can be microencapsulated into a matrix, such as a biodegradable polymer, for example polylactide-polyglycolide. Alternatively, the aripiprazole or prodrug of aripiprazole can be entrapped in the liposomes or in a micro-emulsion compatible with body tissues.

The patient with impaired CYP2D6 or CYP3A4 enzyme function can be a CYP2D6 poor metabolizer, a CYP3A4 poor metabolizer, or both a CYP2D6 poor metabolizer and a CYP3A4 poor metabolizer. In addition, the patient can be schizophrenic, aripiprazole naïve, or both schizophrenic and aripiprazole naïve.

In alternative embodiments, the patient with impaired CYP2D6 or CYP3A4 enzyme function can be a CYP2D6 poor metabolizer, a CYP3A4 poor metabolizer, or both a CYP2D6 poor metabolizer and a CYP3A4 poor metabolizer and concomitantly administered a strong CYP2D6 inhibitor or a strong CYP3A4 inhibitor, or both a strong CYP2D6 and a strong CYP3A4 inhibitor. In still other embodiments, the patient with impaired CYP2D6 or CYP3A4 enzyme function can be an extensive metabolizer (i.e., not a CYP2D6 or CYP3A4 poor metabolizer), and concomitantly administered a strong CYP2D6 inhibitor or a strong CYP3A4 inhibitor, or both a strong CYP2D6 and a strong CYP3A4 inhibitor.

In still other embodiments, the patient with impaired CYP2D6 or CYP3A4 enzyme function can be administered a CYP2D6 or CYP3A4 inducer. CYP3A4 inducers known in the art include carbamezepine, phenytoin, oxcarbazepine, barbiturates such phenobarbital, St. John's Wort, rifampicin, rifabutin, efavirenz, nevirapine, pioglitazone, troglitazone, glucocorticoids, modafinil, etc. CYP2D6 inducers include dexamethasone, rifampicin, glutethimide, etc.

Strong CYP3A4 inhibitors are known in the art, and include aminodarone, anastrozole, azithromycin, cannabinoids, cimetidine, clarithromycin, clotrimazole, cyclosorine, danazol, delavirdine, dexamethasone, diethyldithiocarbamate, diltiazem, dirithryromycin, disulfiram, ethinyl estradiol, fluconazole, fluoxetine, fluoaxamine, gestodene, grapefruit juice, indinavir, isoniazid, ketoconazole, metronidazole, mibefradil, miconazole, nefazodone, nelfinavir, nevirapine, norfloxacin, norfluoxetine, omeprazole, oxiconazole, propoxyphene, quinine, quinupristine, ranitidine, ritonavir, saquinavir, sertindole, sertraline, troglitazone, troleandomycin, valproic acid, etc. Moderate CYP3A4 inhibitors include erythromycin and grapefruit juice.

Strong CYP2D6 inhibitors are also known in the art, and include amiodarone, celecoxib, choroquine, chlorpromazine, cimetidine, citalopram, codeine, deiavirdine, desipramine, dextropropoxyphene, diltiazam, doxorubicin, fluoxetine, fluphenazine, fluvoxamine, haloperidol, labetalol, lobeline, lomustine, methadone, mibefradil, moclobemide, nortuloxeline, paroxetine, propafenone, quinacrine, quinidine, ranitidine, ritonavir, serindole, thioridazine, valproic acid, vinblastine, vincristine, vinorelbine, yohimbine, etc.

The patient with impaired CYP2D6 and/or CYP3A4 enzyme function can be coadministered an oral antipsychotic after administration of the starting dose of the long-acting drug-containing suspension which provides aripiprazole systemically, for example for at least the first 14 days after administration of the starting dose. The oral antipsychotic can comprise aripiprazole, such as about 10 mg per day or about 20 mg per day of aripiprazole. As discussed above, a steady state level of aripiprazole may not be reached until several weeks or months after the starting dose of the long-acting drug-containing suspension which provides aripiprazole systemically is administered. Thus, coadministration of an oral antipsychotic, such as oral aripiprazole, can be helpful to raise the patient's plasma levels of aripiprazole shortly after initiating treatment.

The starting dose of the long-acting drug-containing suspension which provides aripiprazole systemically can contain aripiprazole or a prodrug thereof, and can provide therapeutic plasma levels of aripiprazole for about one month. After about one month, the patient can be maintained on a monthly maintenance dose of a long-acting aripiprazole-releasing suspension, which can be the same as or different from the long-acting aripiprazole-releasing suspension used to administer the starting dose. For example, the maintenance dose can be administered intramuscularly. The maintenance dose of a long-acting aripiprazole-releasing suspension can systemically release a predefined amount of aripiprazole in each dose, for example, no more than 400 mg of aripiprazole per dose.

Example 1

A long-acting aripiprazole-releasing suspension was manufactured as follows. A microparticulate dispersion of aripiprazole was prepared using a DYNO®-MILL (Type KDLA, manufactured by Willy A. Bachoffen AG Maschinefabrik, Basel, Switzerland). The ingredients of Table 1 were added to a 3 L glass jacketed vessel maintained at 15° C. (±5° C.) to form a sterile primary suspension.

TABLE 1

| Component | Mass |
|---|---|
| Aripiprazole | 100 g |
| Sodium carboxymethyl cellulose 7L2P | 9.2 g |
| Mannitol | 45 g |
| Sodium phosphate monobasic | 0.9 g |
| Sodium hydroxide solution, 1N | q.s. to adjust pH to 7.0 |
| Water for injection | q.s. to 1040 g |

The primary suspension was mixed at 500-1,000 rpm for about 0.5 hours and then at 300-500 rpm for an additional 1 hour under a vacuum of 20" Hg (±5" Hg).

A media mill was prepared for media milling. The grinding container was partially filled with zirconium oxide beads and the dispersion was passed through the mill at the following a suspension flow rate of 10 Uh with a milling time of 6 minutes.

2.5 mL of the resulting milled suspension were aseptically filled into sterilized vials which were then aseptically partially stoppered with sterilized stoppers. The vials were aseptically transferred to a freeze dryer and lyophilized according to the following cycle:
  (a) thermal treatment: freeze product at −40° C. over 0.1-1 h and maintain at −40° C. for at least 3 h;
  (b) cool the condenser to −50° C. or below;
  (c) primary drying: lower the chamber pressure to about 100 microns Hg and increase the product temperature to −5° C. over about 2 hours, then maintain primary drying for at least 48 hours;
  (d) stopper the vials under atmospheric pressure or partial vacuum using sterile nitrogen or air and remove from the freeze dryer; and
  (e) seal the vials with appropriate seals and label them.

Example 2

A patient who is a CYP2D6 poor metabolizer is administered a starting dose of aripiprazole by intramuscularly injecting a long-acting suspension comprising the aripiprazole prodrug (7-(4-(4-(2,3-dichlorophenyl)piperazin-1-yl)butoxy)-2-oxo-3,4-dihydroquinolin-1(2H)-yl)methyl dodecanoate, a vehicle, and water into a gluteal muscle. The starting dose contains sufficient (7-(4-(4-(2,3-dichlorophenyl)piperazin-1-yl)butoxy)-2-oxo-3,4-dihydroquinolin-1(2H)-yl)methyl dodecanoate to provide a therapeutic concentration of aripiprazole that is between 66% and 75% of the recommended initial dose for a patient with normal CYP2D6 and CYP3A4 enzyme function. After one month, a maintenance dose is delivered intramuscularly by way of intramuscular injection of a second dose of long-acting drug-containing suspension comprising (7-(4-(4-(2,3-dichlorophenyl)piperazin-1-yl)butoxy)-2-oxo-3,4-dihydroquinolin-1(2H)-yl)methyl dodecanoate. The maintenance dose has sufficient (7-(4-(4-(2,3-dichlorophenyl)piperazin-1-yl)butoxy)-2-oxo-3,4-dihydroquinolin-1(2H)-yl)methyl dodecanoate to systemically deliver about 400 mg of aripiprazole over about one month.

I claim:

1. A method of treating schizophrenia or bipolar I disorder in a patient comprising:
  intramuscularly administering to the patient a long-acting suspension of an adjusted dose of aripiprazole of about 300 mg and co-administering to the patient an oral antipsychotic after a first administration of said adjusted dose of the long-acting suspension,
  wherein the dose is systemically released over a period of about one month and the patient is a CYP2D6 poor metabolizer.

2. The method according to claim 1, wherein the oral antipsychotic is administered at least for 14 days after the first administration of the adjusted dose of the long-acting suspension.

3. The method according to claim 1, wherein the oral antipsychotic is 10 mg or 20 mg per day of aripiprazole.

4. The method according to claim 1, wherein the co-administration of the oral antipsychotic helps achieving a steady state level of aripiprazole after the first administration of the adjusted dose.

5. The method according to claim 1, wherein the step of intramuscularly administering is in the patient's deltoid or gluteal muscle.

6. The method according to claim 1, wherein a long-acting suspension comprises the adjusted dose of aripiprazole, a solvent for injection, and a vehicle for aripiprazole.

7. The method according to claim 6, wherein the vehicle for aripiprazole comprises one or more of at least one suspending agent, at least one bulking agent, at least one buffer, and at least one pH adjusting agent.

8. The method according to claim 7, wherein the suspending agent is carboxymethyl cellulose sodium and the bulking agent is mannitol.

9. The method according to claim 1, wherein the aripiprazole has a mean particle size of about 1 to about 30 microns.

10. A method of treating schizophrenia or bipolar I disorder in a patient comprising:
  intramuscularly administering to the patient a long-acting suspension of an adjusted dose of aripiprazole of about 300 mg and co-administering to the patient an oral antipsychotic after a first administration of said adjusted dose of the long-acting suspension,
  wherein the dose is systemically released over a period of about one month,
  the patient is a CYP2D6 poor metabolizer,
  the oral antipsychotic is administered at least for 14 days after the first administration of the adjusted dose of the long-acting suspension,
  the oral antipsychotic is 10 mg or 20 mg of aripiprazole, and
  the step of intramuscularly administering is in the patient's deltoid or gluteal muscle.

11. The method according to claim 10, wherein a long-acting suspension comprises the adjusted dose of aripiprazole, a solvent for injection, and a vehicle for aripiprazole.

12. The method according to claim 11, the vehicle for aripiprazole comprises one or more of at least one suspending agent, at least one bulking agent, at least one buffer, and at least one pH adjusting agent.

13. The method according to claim 12, wherein the co-administration of the oral antipsychotic helps achieving a steady state level of aripiprazole after the first administration of the adjusted dose.

14. The method according to claim 13, wherein the suspending agent is carboxymethyl cellulose sodium and the bulking agent is mannitol.

15. The method according to claim 14, wherein the aripiprazole has a mean particle size of about 1 to about 30 microns.

16. A method of treating schizophrenia or bipolar I disorder in a patient comprising:
  intramuscularly administering to the patient a long-acting suspension of an adjusted dose of aripiprazole of 300 mg or 200 mg and co-administering to the patient an oral antipsychotic after a first administration of said adjusted dose of the long acting suspension,
  wherein the dose is systemically released over a period of about one month, and the patient has concomitant use of a strong CYP2D6 or CYP3A4 inhibitor.

17. The method according to claim 16, wherein the oral antipsychotic is administered at least for 14 days after the first administration of the adjusted dose of the long-acting suspension.

18. The method according to claim 16, wherein the oral antipsychotic is 10 mg or 20 mg per day of aripiprazole.

19. The method according to claim 16, wherein the co-administration of the oral antipsychotic helps achieving a steady state level of aripiprazole after the first administration of the adjusted dose.

20. The method according to claim 16, wherein the step of intramuscularly administering is in the patient's deltoid or gluteal muscle.

21. The method according to claim 16, wherein a long-acting suspension comprises the adjusted dose of aripiprazole, a solvent for injection, and a vehicle for aripiprazole.

22. The method according to claim 21, wherein the vehicle for aripiprazole comprises one or more of at least one suspending agent, at least one bulking agent, at least one buffer, and at least one pH adjusting agent.

23. The method according to claim 22, wherein the suspending agent is carboxymethyl cellulose sodium and the bulking agent is mannitol.

24. The method according to claim 16, wherein the aripiprazole has a mean particle size of about 1 to about 30 microns.

25. A method of treating schizophrenia or bipolar I disorder in a patient comprising:
   intramuscularly administering to the patient a long-acting suspension of an adjusted dose of aripiprazole of 300 mg or 200 mg and co-administering to the patient an oral antipsychotic after a first administration of said adjusted dose of the long acting suspension,
   wherein the dose is systemically released over a period of about one month,
   the patient has concomitant use of a strong CYP2D6 or CYP3A4 inhibitor,
   the oral antipsychotic is administered at least for 14 days after the first administration of the adjusted dose of the long-acting suspension,
   the oral antipsychotic is 10 mg or 20 mg of aripiprazole, and
   the step of intramuscularly administering is in the patient's deltoid or gluteal muscle.

26. The method according to claim 25, wherein a long-acting suspension comprises the adjusted dose of aripiprazole, a solvent for injection, and a vehicle for aripiprazole.

27. The method according to claim 26, the vehicle for aripiprazole comprises one or more of at least one suspending agent, at least one bulking agent, at least one buffer, and at least one pH adjusting agent.

28. The method according to claim 27, wherein the co-administration of the oral antipsychotic helps achieving a steady state level of aripiprazole after the first administration of the adjusted dose.

29. The method according to claim 28, wherein the suspending agent is carboxymethyl cellulose sodium and the bulking agent is mannitol.

30. The method according to claim 29, wherein the aripiprazole has a mean particle size of about 1 to about 30 microns.

* * * * *